(12) United States Patent
Rockrohr

(10) Patent No.: US 8,070,730 B2
(45) Date of Patent: Dec. 6, 2011

(54) INTEGRAL INSUFFLATION VALVE

(75) Inventor: Brian Rockrohr, Waterbury, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/712,652

(22) Filed: Feb. 25, 2010

(65) Prior Publication Data
US 2010/0249695 A1    Sep. 30, 2010

Related U.S. Application Data

(60) Provisional application No. 61/164,035, filed on Mar. 27, 2009.

(51) Int. Cl.
*A61M 5/178* (2006.01)

(52) U.S. Cl. .. 604/167.05; 604/23; 604/26; 604/167.01; 604/248

(58) Field of Classification Search .............. 604/23, 604/26, 167.01, 167.03, 167.05, 246, 248; 251/297, 352

See application file for complete search history.

(56) References Cited

U.S. PATENT DOCUMENTS

| | | |
|---|---|---|
| 2,261,213 A | 11/1941 | Bierman |
| 2,711,740 A | 6/1955 | Pickens |
| 3,362,400 A | 1/1968 | De Bella |
| 3,467,082 A | 9/1969 | Gilbert |
| 3,776,229 A | 12/1973 | McPhee |
| 3,777,737 A | 12/1973 | Bucalo |
| 3,794,032 A | 2/1974 | Derouineau |
| 3,834,372 A | 9/1974 | Turney |
| 3,926,187 A | 12/1975 | Iglesias |
| 4,553,964 A | 11/1985 | Sasaki |
| 4,648,868 A | 3/1987 | Hardwick et al. |
| 4,758,235 A | 7/1988 | Tu |
| 4,966,551 A | 10/1990 | Betush |
| 5,019,054 A | 5/1991 | Clement et al. |
| 5,074,334 A | 12/1991 | Onodera |
| 5,578,016 A | 11/1996 | Zinger |
| 5,817,068 A | 10/1998 | Urrutia |
| 5,832,959 A | 11/1998 | Szymczakowski et al. |

(Continued)

FOREIGN PATENT DOCUMENTS

EP    2 133 032    12/2009

(Continued)

OTHER PUBLICATIONS

European Search Report for EP 10 25 0606 date of completion is Jun. 21, 2010 (3 pages).

*Primary Examiner* — Bhisma Mehta

(57) ABSTRACT

A trocar assembly includes a trocar valve body defining a cavity. The assembly includes a rotatable valve handle that is elongated and has a first end and a second end. The first end is sized and configured to be rotatably maintained within the cavity and the second end extends outwardly so as to be actuatable by a user. The rotatable valve handle defines a lumen therethrough which extends longitudinally from the first end to the second end. The valve body defines an outlet that communicates with the cavity. The rotatable valve handle is rotatable from an open position, in which the lumen is at least partially aligned with the outlet so as permit fluid to pass through the lumen, and a closed position, in which the lumen is not aligned with the outlet so as prevent fluid to pass through the lumen.

2 Claims, 3 Drawing Sheets

U.S. PATENT DOCUMENTS

| | | | |
|---|---|---|---|
| 5,836,924 A * | 11/1998 | Kelliher et al. | 604/248 |
| 5,865,812 A | 2/1999 | Correia | |
| 6,099,511 A | 8/2000 | Devos et al. | |
| 7,172,572 B2 | 2/2007 | Diamond et al. | |
| 7,232,420 B1 | 6/2007 | Abulhaj | |
| 7,232,428 B1 | 6/2007 | Inukai et al. | |
| 2001/0025942 A1 | 10/2001 | Lotz et al. | |
| 2007/0088277 A1 * | 4/2007 | McGinley et al. | 604/167.01 |

FOREIGN PATENT DOCUMENTS

| | | |
|---|---|---|
| WO | WO 2004/032770 | 4/2004 |
| WO | WO 2007/048083 | 4/2007 |

* cited by examiner

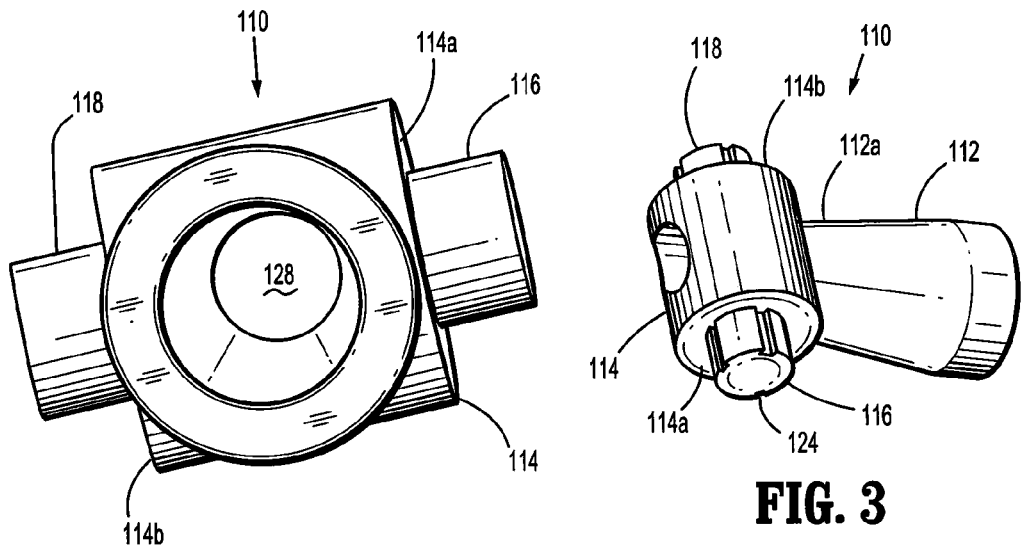
FIG. 4
FIG. 3
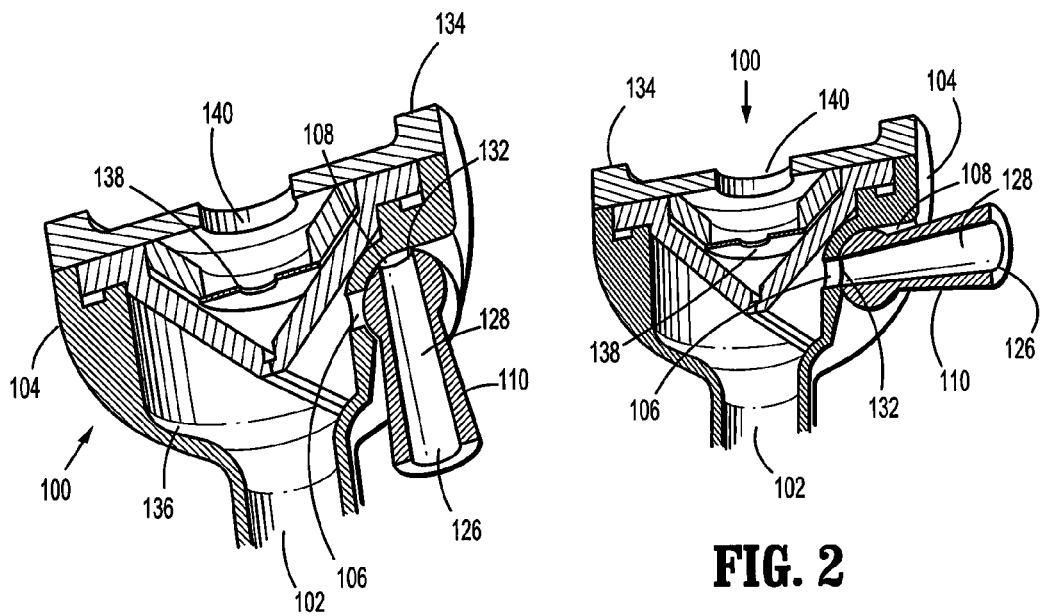
FIG. 1
FIG. 2

INTEGRAL INSUFFLATION VALVE

CROSS REFERENCE TO RELATED APPLICATION

The present application claims the benefit of and priority to U.S. Provisional Application Ser. No. 61/164,035 filed on Mar. 27, 2009, the entire contents of which are incorporated herein by reference.

BACKGROUND

1. Technical Field

The present disclosure relates generally to a valve and, more particularly, to a selectively rotatable valve configured and dimensioned to control the flow of insufflation gases through an access port.

2. Background of Related Art

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

One of the advances in recent years to reduce the invasiveness of surgical procedures is endoscopic surgery. Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions.

Insufflatory surgery involves filling a body cavity with a pressurized gas or other biocompatible fluid to expand or to maintain the cavity under certain predetermined pressure and to facilitate access to one or more organs or surgical sites. One way of performing the surgery is by first puncturing the skin using a trocar in a desired body cavity region and introducing an insufflation gas into the body cavity to inflate it.

SUMMARY

The present disclosure relates to a housing for controlling fluid flow from a fluid source to an outlet. The housing has a fluid source for supplying fluids, in some instances, insufflation gases. The housing includes a body having at least one outlet and a cavity. A selectively rotatable integral valve is disposed in the cavity and configured and dimensioned to be rotated in a receded configuration. The integral valve has a handle and a regulator. A lumen is disposed along the longitudinal axis of the integrally connected handle and regulator. A user controls the fluid flow between the fluid source and the outlet by articulating the integral valve to predetermined positions, enabling or inhibiting the flow of fluids from the fluid source into the outlet. It is envisioned that this housing can be used for insufflation purposes.

A pair of protuberances is disposed in mirror image along the longitudinal axis of the regulator on opposing surfaces of the regulator for engaging a pair of bores disposed in the cavity. As a user articulates the handle, the protuberances rotate within the bores. At least one of the protuberances has at least one detent longitudinally disposed along the radial surface for affixing the integral valve in a predetermined location. A plurality of detents for affixing the integral valve in a plurality of predetermined locations is also contemplated. The predetermined positions are indicative of various flow rates, enabling the user to adjust or otherwise control the flow of fluid through the housing. As such, the user can selectively control fluid flow through opened, partially opened, or closed positions.

In an embodiment of the present invention, there is provided a trocar assembly that comprises a trocar valve body defining a cavity, the valve body for communicating insufflation fluid therethrough. The assembly also comprises a selectively rotatable valve handle for controlling a flow of said insufflation fluid through the valve body. The rotatable valve handle is elongated and has a first end and a second end. The first end is sized and configured to be rotatably maintained within the cavity and the second end extends outwardly so as to be actuatable by a user. The rotatable valve handle defines a bore therethrough which extends longitudinally from the first end to the second end. The valve body defines an outlet that communicates with the cavity. The rotatable valve handle is rotatable from an open position, in which the bore of the valve is at least partially aligned with the outlet so as permit fluid to pass through the bore, and a closed position, in which the bore of the valve is not aligned with the outlet so as prevent fluid to pass through the bore. The rotatable valve handle has at its first end a protuberance that engages a valve body bore of the valve body, the protuberance assisting with maintaining the rotatable valve handle within the cavity. A first one of the valve body bore and the protuberance may include a detent, and a second one of the valve body bore and the protuberance may include a ridge, the ridge configured to engage the detent so as to maintain the rotatable valve handle in position relative to the valve body. The trocar assembly may include multiple valve body bore and/or ridges, such that the rotatable valve handle may be selectively maintained in various different positions relative to the valve body.

BRIEF DESCRIPTION OF THE DRAWINGS

The above and other aspects, features, and advantages of the presently disclosed integral insufflation valve will become more apparent in light of the following detailed description when taken in conjunction with the accompanying drawings in which:

FIG. 1 is a front cross-sectional perspective view of a portion of a trocar assembly with an integral valve, the integral valve shown in a closed configuration in accordance with the present disclosure;

FIG. 2 is a front cross-sectional perspective view of the trocar assembly of FIG. 1 with the integral valve shown in an open configuration;

FIG. 3 is a side perspective view of an integral valve in accordance with the present disclosure;

FIG. 4 is a bottom perspective view of FIG. 3;

DETAILED DESCRIPTION OF THE EMBODIMENTS

Figure 5:
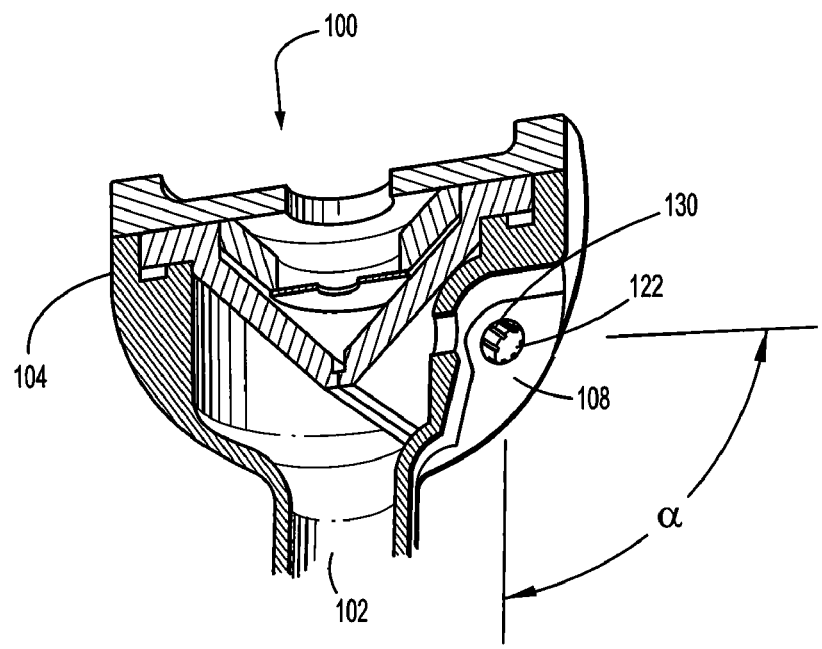
FIG. 5 is a front cross-sectional perspective view of the trocar assembly of FIGS. 1 and 2 with the integral valve removed for clarity.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

Figure 6:
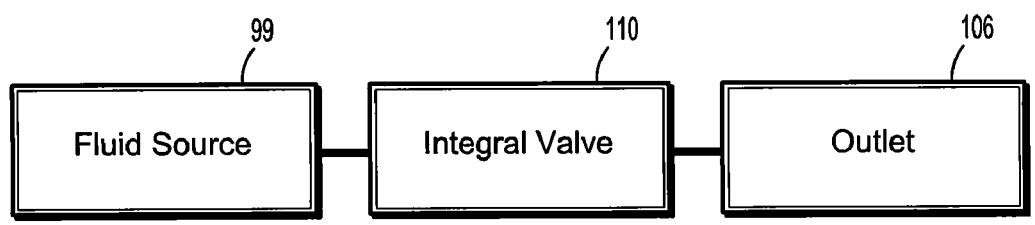
FIG. 6 is a diagrammatical view of one embodiment of a housing of the trocar assembly of FIGS. 1 and 2 in accordance with the present disclosure.

Referring now to the drawings, in which like reference numerals identify identical or substantially similar parts throughout the several views. FIGS. 1 and 2 illustrate one embodiment in accordance with the present disclosure. A housing 100 includes a body 104 having a cap 134 at one end and a cannula 102 at an opposing end. The housing 100 includes a duck bill seal 136 and an instrument seal 138. Instruments are insertable through an opening 140 in the cap 134. The housing 100 further includes an integral valve 110 disposed in a cavity 108 of the housing 100. As seen in FIG. 6, the housing 100 further includes a fluid source 99 for supplying fluids. The body 104 has at least one outlet 106. Illustrated in FIGS. 3 and 4, the integral valve 110 defines a lumen 128 therethrough and is selectively rotatable. The diameter of the lumen 128 decreases distally wherein the lumen 128 has an inlet 126 at the proximal end thereof and an opening 132 at the distal end thereof.

The integral valve 110 includes a handle 112 and a regulator 114, each of which has a substantially cylindrical shape. The handle 112, however, has a tapered distal portion 112a. The handle 112 is integrally connected to the regulator 114. The tapered distal portion 112a of the handle 112 abuts the curved outer surface of the regulator 114. As such, the regulator 114 is disposed at a substantially orthogonal orientation relative to the handle 112. The regulator 114 is configured and dimensioned to inhibit or enable fluid flow upon predetermined articulation of the handle 112. The integral valve 110 is selectively rotatable within the cavity 108. As such, an end user can control fluid flow between the fluid source 99 and the at least one outlet 106 by the integral valve 110 (FIG. 6). In some manifestations, the housing 100 is configured and dimensioned to control insufflation gases traveling therethrough.

Figure 7:
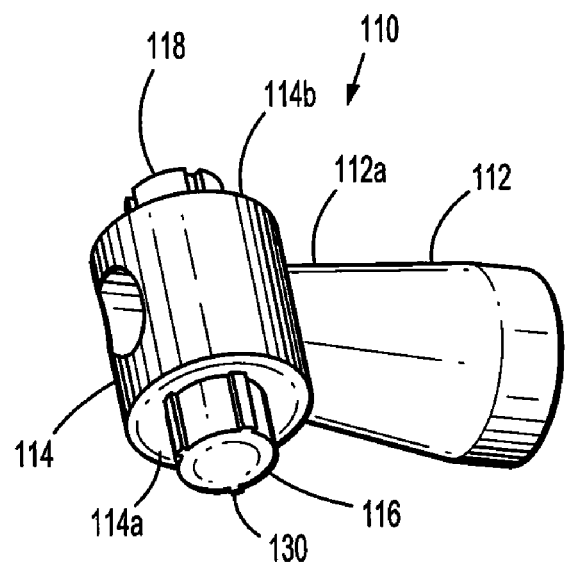
FIG. 7 is a side perspective view of another embodiment of an integral valve in accordance with the present disclosure.
Figure 8:
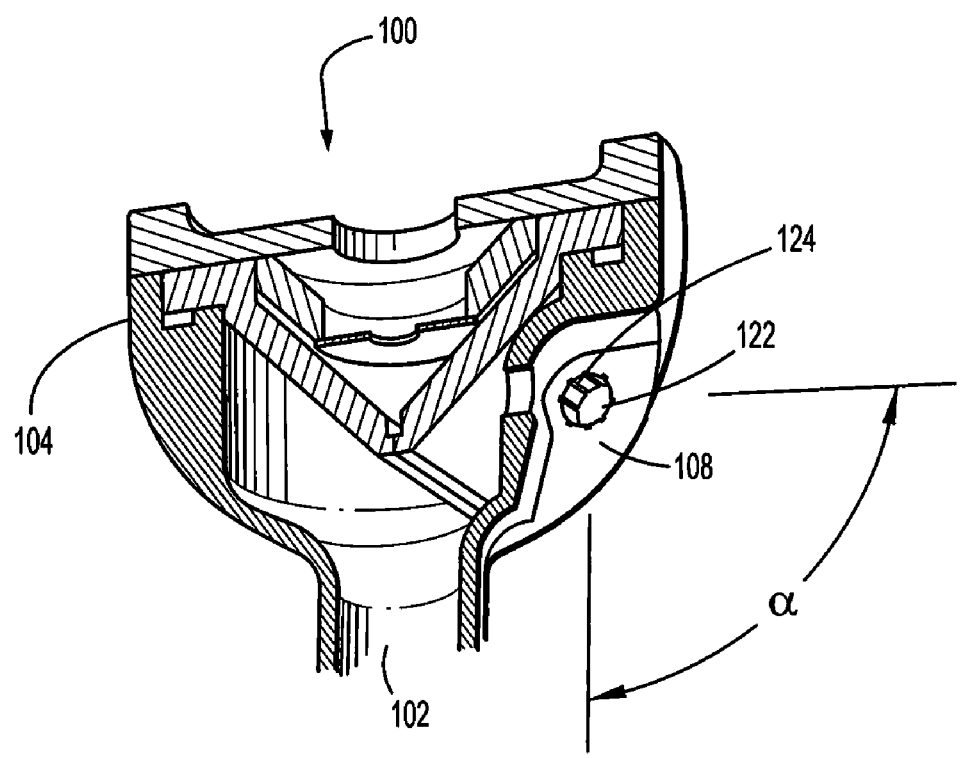
FIG. 8 is a front cross-sectional perspective view of another embodiment of a housing of the trocar assembly of FIGS. 1 and 2 with the integral valve removed for clarity.

As shown in FIGS. 3 and 4, the integral valve 110 has a pair of protuberances 116, 118 disposed on the regulator 114. Furthermore, FIG. 5 is a cross-sectional view of the housing 100 showing one section of the housing 100 which illustrates one bore 122 of a pair of bores defined within the housing 100. The other bore 122 of the pair of bores is defined in a second section (not shown) of the housing 100 which is substantially similar to the section of the housing 100 illustrated in FIG. 5. Each bore 122 is disposed in the cavity 108 relative to each respective section of the housing 100. The pair of protuberances 116, 118 is rotatably mounted in the pair of bores. Each of the pair of protuberances 116, 118 is disposed in mirror image of each other along the longitudinal axis of the regulator 114 on the opposing surfaces 114a, 114b of the regulator 114. At least one of the protuberances 116, 118 includes at least one detent 124 longitudinally disposed along the radial surface thereof. At least one of the bores 122 includes at least one ridge 130, in some instances a plurality of ridges 130, disposed radially along the surface of the bore 122 (FIG. 5). As can be appreciated, at least one of the bores 122 may include at least one detent 124 (see FIG. 8) and at least one of the protuberances 116, 118 may include at least one ridge 130 (see FIG. 7). Each detent 124 is configured and dimensioned to engage at least one ridge 130, or a plurality of ridges 130.

In the embodiment shown in FIG. 3, the protuberances 116, 118 include a plurality of detents 124 longitudinally disposed along the radial surface of each. Each detent 124 is configured and dimensioned to hold the integral valve 110 in a predetermined position. Each predetermined position is indicative of a predetermined flow rate. Furthermore, the integral valve 110 is selectively positionable between a plurality of positions including an opened position, a partially opened position, and a closed position. As such, the integral valve 110 is selectively rotatable into a receded configuration as illustrated in FIG. 1. The housing 100 is configured and dimensioned to enable fluid flow through the housing 100 when the integral valve 110 is positioned in either the opened position or the partially opened position (FIG. 2). Conversely, the housing 100 is also configured and dimensioned to inhibit fluid flow through the housing 100 when the integral valve 110 is positioned in the closed position (FIG. 1). As shown in FIG. 2, the lumen 128 and the outlet 106 can be arranged in substantially concentric alignment. Alternatively, the lumen 128 and the outlet 106 can also be arranged in substantially orthogonal alignment, as shown in FIG. 1. Further, the lumen 128 and the outlet 106 are configured and dimensioned to be disposed at an angle alpha ($\alpha$) relative to each other. The range of angle alpha ($\alpha$) is defined between about concentric alignment of the lumen 128 and the outlet 106 and about orthogonal alignment of the lumen 128 and the outlet 106 (FIG. 5).

In operation, a user rotates the integral valve 110 by the handle 112 to a predetermined position to control the flow of fluids. Each detent 124 engages the respective bore 122 of the pair of bores and removably affixes to the predetermined position upon user selection. Upon rotation into an open or partially opened configuration, the fluid source 99 attached to the handle 112 passes fluid, in some instances insufflation gases, through the inlet 126 disposed on the proximal end of the handle 112. In this configuration, the handle 112 juts out, indicating fluid flow passage. The fluid travels through the lumen 128 and the regulator 114 and out of the opening 132 at the distal end of the integral valve 110. In the opened or partially opened configuration, the fluids pass into the outlet 106 and down through a cannula 102 and into a patient's body. When the user rotates the integral valve 110 into the closed configuration, the regulator 114 prevents the flow of the fluids through the outlet 106. In the closed configuration, the handle 112 is positioned so that it is in a receded and in an "out of the way" position, preventing unwanted snagging and providing a means for indicating fluid flow stoppage.

While various advantages of this arrangement have been described herein above, it should be further appreciated that the present invention may simplify the manufacturability of valve bodies by reducing the number of components typically needed for such an insufflation-type valve. Furthermore, the present invention may be particularly well-suited for applications in which it is desirable to have a relatively small, or low profile, valve body, since typical insufflation-type valve arrangements, which tend to extend radially outward from a valve body a significant distance therefrom (irrespective of whether open or closed), may undesirably interfere with each other during a surgical procedure when such valve bodies are positioned in close proximity to each other. In some embodiments of the present invention (and as shown in FIG. 2), when the rotatable valve handle is in the closed position, it may avoid extending beyond an overall outer circumference of the valve body. In this manner, the valve handles may be out of the way and may suffer minimal interference with each other when valve bodies are positioned adjacent to or in direct contact with each other during a surgical procedure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A trocar assembly comprising:
a trocar valve body defining a cavity, the valve body for communicating insufflation fluid therethrough; and
a selectively rotatable valve handle for controlling a flow of said insufflation fluid through the valve body, the rotatable valve handle being elongated and having a first end and a second end, the rotatable valve handle defining a lumen therethrough which extends longitudinally from the first end to the second end to communicate insufflation fluid between the first end and the second end, the first end sized and configured to be rotatably maintained within the cavity and the second end extending outwardly so as to be actuatable by a user;
wherein the valve body defines an outlet that communicates with the cavity;
wherein the rotatable valve handle is rotatable from an open position, in which the lumen of the rotatable valve handle is at least partially aligned with the outlet so as permit fluid to pass through the lumen, and a closed position, in which the lumen is not aligned with the outlet so as to prevent fluid to pass through the lumen;
wherein the rotatable valve handle has at its first end a protuberance that engages a bore defined in the valve body, the protuberance assisting with maintaining the rotatable valve handle within the cavity;
wherein one of the bore and the protuberance includes a detent, the other of the bore and the protuberance includes a ridge, the ridge configured to engage the detent so as to maintain the rotatable valve handle in position relative to the valve body.

2. The trocar assembly of claim 1, wherein one of the bore and the protuberance includes a plurality of detents, the other of the bore and the protuberance includes a plurality of ridges, the plurality of ridges configured to engage the plurality of detents to selectively maintain the rotatable valve handle in various different positions relative to the valve body.

\* \* \* \* \*